(12) United States Patent
Dudding et al.

(10) Patent No.: US 9,675,079 B1
(45) Date of Patent: Jun. 13, 2017

(54) PATHOGEN ELIMINATING ARTICLE

(71) Applicants: Jeffery L. Dudding, Center, MO (US); Amod P. Paranjpe, Augusta, MO (US)

(72) Inventors: Jeffery L. Dudding, Center, MO (US); Amod P. Paranjpe, Augusta, MO (US)

(73) Assignee: CLAW Biotech Holdings LLC, Des Peres, MO (US)

( * ) Notice: Subject to any disclaimer, the term of this patent is extended or adjusted under 35 U.S.C. 154(b) by 0 days.

(21) Appl. No.: 15/184,556

(22) Filed: Jun. 16, 2016

(51) Int. Cl.
| | | |
|---|---|---|
| *A01N 59/16* | (2006.01) | |
| *B65D 81/28* | (2006.01) | |
| *A01N 25/26* | (2006.01) | |
| *C22C 27/04* | (2006.01) | |
| *B65D 43/02* | (2006.01) | |

(52) U.S. Cl.
CPC .............. *A01N 59/16* (2013.01); *A01N 25/26* (2013.01); *B65D 43/02* (2013.01); *B65D 81/28* (2013.01); *C22C 27/04* (2013.01)

(58) Field of Classification Search
CPC ........ A01N 59/16; A01N 25/26; B65D 43/02; B65D 81/28; C22C 27/04; Y10T 428/14
See application file for complete search history.

(56) References Cited

U.S. PATENT DOCUMENTS

| | | |
|---|---|---|
| 3,966,426 A | 6/1976 | McCoy et al. |
| 4,646,935 A | 3/1987 | Ulam |
| 6,267,830 B1 | 7/2001 | Groll |
| 6,929,705 B2 * | 8/2005 | Myers ............... A01N 25/34 106/813 |
| 7,488,444 B2 * | 2/2009 | Furst ................ B22F 3/16 148/423 |
| 7,906,221 B2 | 3/2011 | Groll |
| 8,133,596 B2 | 3/2012 | Groll |
| 8,609,036 B2 | 12/2013 | Fuller et al. |
| 8,778,408 B2 | 7/2014 | Hirota et al. |
| 9,162,013 B2 * | 10/2015 | Guggenbichler ...... A01N 59/16 |
| 2010/0061884 A1 | 3/2010 | Clark et al. |
| 2012/0225312 A1 | 9/2012 | Chin et al. |
| 2014/0224519 A1 | 8/2014 | Mallak et al. |
| 2015/0086597 A1 | 3/2015 | Mallak et al. |
| 2015/0290042 A1 * | 10/2015 | Freer .................. A61F 13/0213 602/43 |

FOREIGN PATENT DOCUMENTS

| | | |
|---|---|---|
| CN | 201055998 Y | 5/2008 |
| CN | 103911540 A | 7/2014 |
| WO | 2012045308 A1 | 4/2012 |

OTHER PUBLICATIONS

Hobman et al., Bacterial antimicrobial metal ion resistance, Journal of Medical Microbiology, dated Nov. 2014, pp. 471-497.
Romanszki et al., Polystyrene films as barrier layers for corrosion protection of copper and copper alloys, Bioelectrochemistry, dated 2014, pp. 7-14.
Research reveals 'halo' effect of copper surfaces, http://ww.cleanroomtechnology.com, date retrieved Jun. 24, 2015, pp. 2.

\* cited by examiner

*Primary Examiner* — Patricia L Nordmeyer
(74) *Attorney, Agent, or Firm* — Armstrong Teasdale LLP

(57) ABSTRACT

An antimicrobial article includes a first surface and an opposing second surface. The antimicrobial core is formed from an antimicrobial alloy comprising at least 50% molybdenum such that the antimicrobial alloy is configured to eliminate pathogens located proximate the first and second surfaces.

16 Claims, 2 Drawing Sheets

PATHOGEN ELIMINATING ARTICLE

BACKGROUND

The present disclosure is directed generally to methods and apparatus related to antimicrobial products for use in neutralizing harmful pathogens and, more particularly, to methods and apparatus having an antimicrobial alloy core including molybdenum.

Currently, there exists a large variety of strains of antibiotic resistant virulent microbes. Such microbes are known to cause a variety of diseases. Microbes like methicillin-resistant *staphylococcus aureus* strain ATCC 6538, which, if left untreated, can lead to sickness and even death. This problem is especially prevalent in locations (hospitals, hotels, public schools, elderly homes, etc.) where infectious microbes can easily be spread among its inhabitants. There is a need to frequently disinfect surfaces that people may come into contact with. Additionally, food manufacturing and preparation facilities are known to house microbes such as *E. Coli* and *Salmonella*. Such microbes may be located on surfaces that contact food items before they are packaged or prepared for human consumption. Accordingly, in order to disinfect surfaces that may harbor such infectious microbes, such surfaces and facilities require frequent cleaning using antimicrobial agents.

At least some known antimicrobial agents include chemical antimicrobial agents, e.g., disinfectants. However, at least some chemical antimicrobial agents may be harmful to both the environment and the person coming into contact with them. Also, at least some chemical antimicrobial agents lose their antimicrobial effectiveness within a relatively short time period as the microbes become resistant to the agent.

BRIEF DESCRIPTION

In one aspect, an antimicrobial article is provided. The antimicrobial article includes a first surface and an opposing second surface. The antimicrobial core is formed from an antimicrobial alloy comprising at least 50% molybdenum such that the antimicrobial alloy is configured to eliminate pathogens located proximate the first and second surfaces.

In another aspect, a storage container is provided. The storage container includes a plurality of walls defining a cavity configured to receive an item to be stored therein. At least one wall of the plurality of walls is formed from an antimicrobial article including an antimicrobial core having a first surface and an opposing second surface. The antimicrobial core is formed from an antimicrobial alloy comprising at least 50% molybdenum such that the antimicrobial alloy is configured to eliminate pathogens located proximate the first and second surfaces within the cavity.

DETAILED DESCRIPTION

Figure 1:
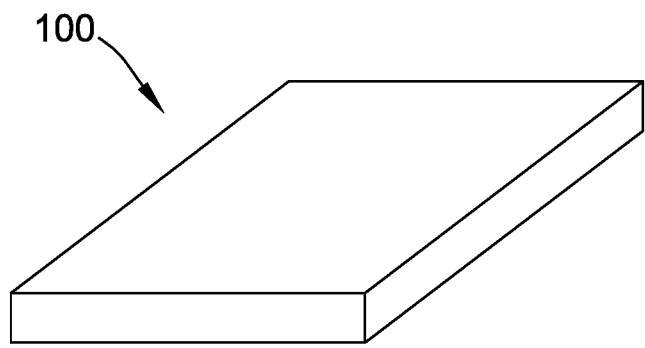
FIG. 1 is a perspective view of an exemplary antimicrobial article.

Described herein is an antimicrobial article including an antimicrobial metallic alloy core. The antimicrobial core includes an antimicrobial alloy containing a minimum of 50% of molybdenum. As described in further detail below, the antimicrobial article provides an antimicrobial property used to disinfect a surface having harmful microbes. The antimicrobial article uses a combination of the "oligodynamic effect" to reduce or eliminate the microbes that directly contact the surface of the alloy and the "impact zone effect" to reduce or eliminate the microbes on surfaces in the proximity of the antimicrobial material due to electromagnetic energy produced by the protected antimicrobial alloy core. Using the "impact zone effect", the antimicrobial article disinfects the environment immediately surrounding the antimicrobial article without contacting the pathogen located thereon and within a relatively short period of time.

Additionally, as used herein, the term "pathogens" is meant to describe any harmful virus, bacteria, or fungus that may cause disease. For example, a pathogen may be any of methicillin-resistant *staphylococcus aureus* strain ATCC 6538, and the like. More specifically, pathogens commonly found in healthcare environments include *Acinetobacter baumannii, Bacteroides fragilis, Burkholderia cepacia, Clostridium difficile, Clostridium sordellii,* Carbapenem-resistant Enterobacteriaceae, *Enterococcus faecalis, Escherichia coli,* Hepatitis A, Hepatitis B, Hepatitis C, Human Immunodeficiency Virus, Influenza, *Klebsiella pneumonia,* Methicillin-resistant *Staphylococcus aureus, Morganella morganii, Mycobacterium abscessus,* Norovirus, *Psuedomonas aeruginosa, Staphylococcus aureus, Stenotrophomonas maltophilia, Mycobacterium tuberculosis,* Vancomyin-resistant *Staphylococcus aureus,* and Vancomycin-resistant Enterococci.

Furthermore, pathogens commonly found in food production that are eliminated by the "oligodynamic effect" and the "impact zone effect" include *Bacillus cereus,* Botulism, *Campylobacter, Clostridium perfringens, E-coli,* Listeria, Norovirus, *Salmonella, Shigella, Vibrio vulnificus* and *Vibrio parahaemolyticus.* Many known pathogens eliminated by the "impact zone effect" may be found in many different environments.

The terms "including", "comprising" and variations thereof, as used in this disclosure, mean "including, but not limited to", unless expressly specified otherwise.

The terms "a", "an", and "the", as used in this disclosure, means "one or more", unless expressly specified otherwise. The terms "about" or "approximately" refer to within +/−10%, when referring to a percentage.

Although process steps, method steps, or the like, may be described in a sequential order, such processes and methods may be configured to work in alternate orders. In other words, any sequence or order of steps that may be described does not necessarily indicate a requirement that the steps be performed in that order. The steps of the processes or methods described herein may be performed in any order that facilitates operation of the method.

Referring now to FIG. 1, a perspective view of an exemplary antimicrobial article 100 is illustrated. Antimicrobial article 100 includes any product used in, for example, healthcare, extended care, residential or commercial facilities, public or private facilities, public or private vehicles, food manufacturing and preparation locations, medical and other health care devices, refrigeration units, HVAC (heating, ventilation and air conditioning) equipment, agriculture (to prevent greening disease and other similar plant pathogens), or anywhere else where pathogens may be transferred through contact of or exposure to a surface.

Figure 2:
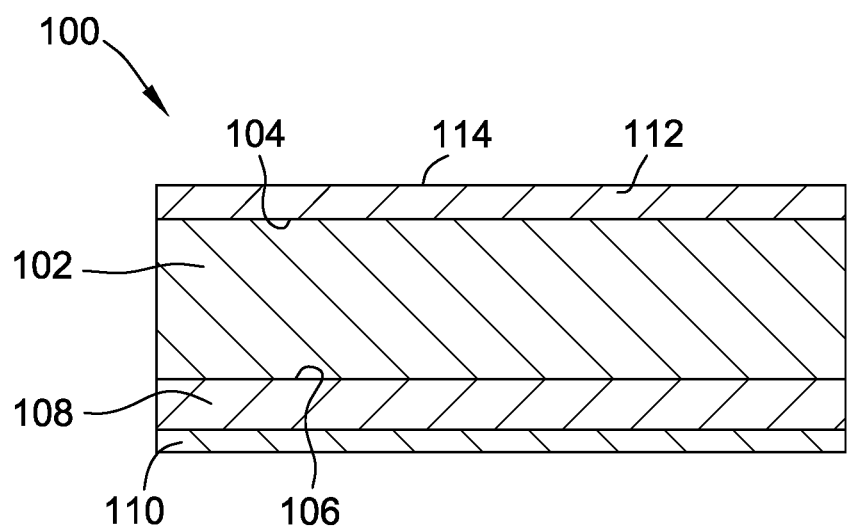
FIG. 2 is a cross-sectional view of the antimicrobial article shown in FIG. 1.
Figure 3:
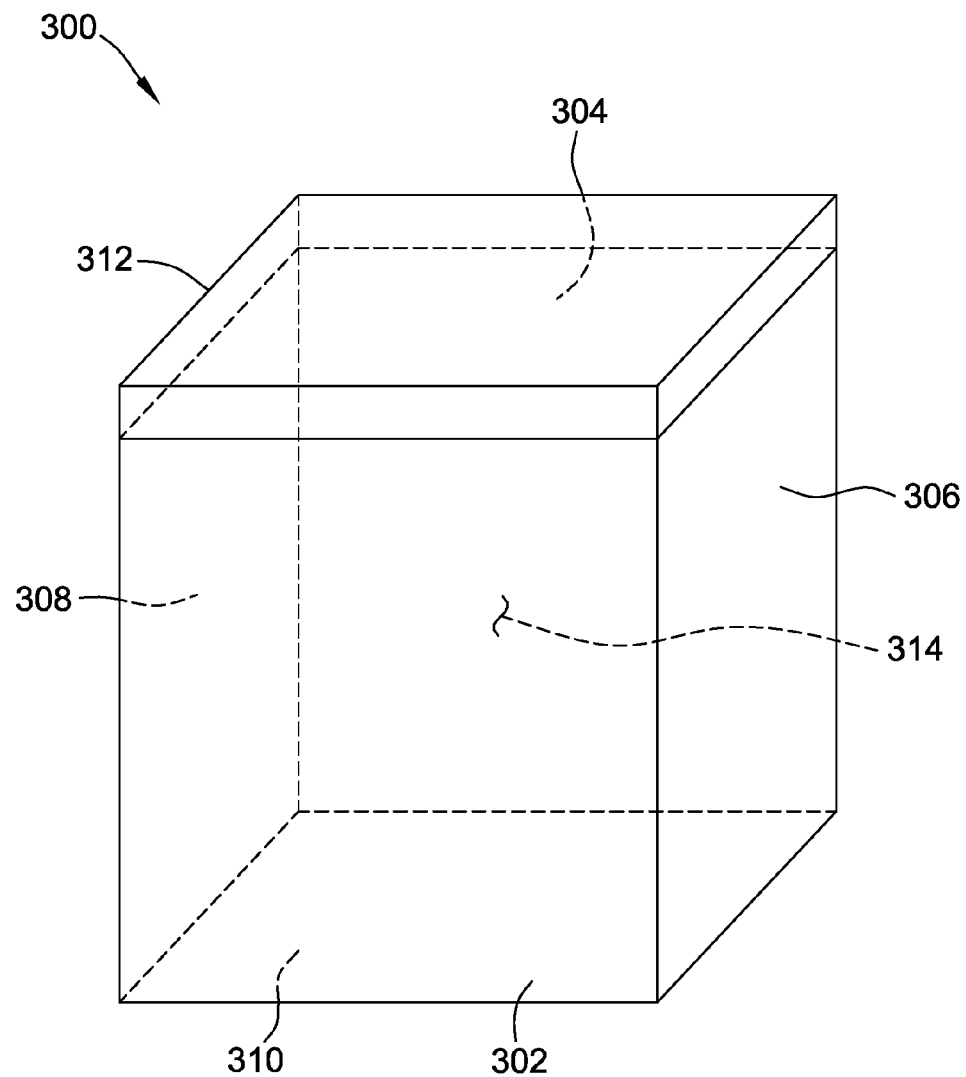
FIG. 3 is a perspective view of a food storage container at least partially formed from the antimicrobial article shown in FIG. 1.

FIG. 2 is a cross-sectional view of antimicrobial article 100. In the exemplary embodiment, antimicrobial article 100 includes only an antimicrobial core 102 having a top surface 104 and a bottom surface 106. As described herein, antimicrobial core 102 is formed from an antimicrobial material that eliminates pathogens located on surfaces 104 and 106 and also eliminates pathogens located within an effective area of core 102 that do not contact surfaces 104 or 106. In one embodiment, article 100 is formed from additive manufacturing, such as but not limited to, electron beam melting, selective laser sintering, direct metal laser sintering, or other similar technologies. More specifically, the material making up article 100 is initially in powder form and is then solidified into a desired shape using one of the techniques listed herein.

In one embodiment, antimicrobial article 100 also includes an adhesive layer 108 coupled to bottom surface 106. Adhesive layer 108 may be coupled to an entire area of bottom surface 106 or only to a portion thereof. In embodiments including adhesive layer 108, antimicrobial article 100 is coupled to an object (not shown) using adhesive layer. Additionally, antimicrobial article 100 includes a removable protective sheeting 110 coupled to adhesive layer 108 opposite core 102. Sheeting 110 is coupled to an exterior of adhesive layer 108 to facilitate protecting adhesive layer 108 prior to use. As such, in operation, sheeting 110 is removed from antimicrobial article 100 to expose adhesive layer 108, which is then used to adhere antimicrobial article 100 to a surface of the object. In such embodiments, core 102 and adhesive layer 108 are formed into a corresponding shape of the object to facilitate optimal bonding of antimicrobial article 100. Alternatively, antimicrobial article 100 does not include adhesive layer 108 or protective sheeting 110.

In the above described embodiment, top surface 104 of core 102 is exposed to the environment such that any potentially harmful bacterium and pathogens coming into contact with top surface 104 are eliminated within a relatively short period of time, for example, within 2 hours of exposure to top surface 104 of core 102 due to the "oligodynamic effect" described herein. Furthermore, the electromagnetic energy produced by the antimicrobial core 102 eliminates potentially harmful bacterium and pathogens within a known distance of antimicrobial core 102 due to the "impact zone effect" described herein.

As shown in FIG. 2, antimicrobial article 100 may also include a protective coating 112 coupled to top surface 104. In one embodiment, coating 112 is similar to sheeting 110 in that coating 112 protects top surface 104 during transport and is removable during or after installation of antimicrobial article 100 to expose top surface 104. In another embodiment, protective coating 112 is permanently coupled to top surface 104 and remains in place during use of antimicrobial article 100. In such embodiments, top surface 104 is not exposed to the environment, and so the "oligodynamic effect" is tempered. However, in such a configuration, the "impact zone effect" antimicrobial property of antimicrobial core 102 emits electromagnetic energy that penetrates protective coating 112 and disinfects an exposed surface 114 thereof without directly contacting the pathogen located on exposed surface 114 within a time period of approximately 2-3 hours at a microbe contamination level of approximately $10^3$ colony-forming units per square centimeter ($CFU/cm^2$).

In the exemplary embodiment, antimicrobial core 102 effectively kills pathogens within approximately 2-3 hours of the pathogens being exposed to antimicrobial core 102 whether through contacting core 102 by the "oligodynamic effect" and through the electromagnetic energy emitted by core by the "impact zone effect". As such, antimicrobial article 100 may be located in any location that is likely to come into contact with or within an estimated effective range of the electromagnetic energy's "impact zone effect". In the exemplary embodiment, experimentation has demonstrated that the "impact zone effect" of antimicrobial core 102 exhibits up to 70% effectiveness against pathogen microbes at a distance of up to 50.0 centimeters (19.68 inches). Furthermore, the effectiveness against pathogen microbes has been shown to be independent of both the material and thickness of protective coating 112.

In the exemplary embodiment, antimicrobial core 102 is fabricated from an antimicrobial alloy including molybdenum. More specifically, antimicrobial core 102 includes an alloy having an antimicrobial active component and a non-antimicrobial inactive component. As described above, the active component includes molybdenum. Additionally, the active component makes up at least 50% of a total material by volume of antimicrobial core 102. More specifically, the active component makes up between approximately 60% to approximately 99% of a total material by volume of antimicrobial core 102. In the exemplary embodiment, the inactive component includes at least one of nickel, zinc, and stainless steel. In another embodiment, the inactive component includes at least one of aluminum, chromium, plastic, wood, concrete, composites including carbon fiber and fiberglass, ceramic, resins including paints and coatings, etc. Some of these inactive components may be used to encase molybdenum core 102, using additive manufacturing technology, to surround core 102 and exploiting its "impact zone effect properties" such as an antimicrobial medical implant device. The inactive component makes up between approximately 1% to approximately 50% of a total material by volume of antimicrobial core 102. For example, in the exemplary embodiment, antimicrobial core 102 includes an alloy of approximately 70% molybdenum and approximately 30% nickel.

FIG. 4 is a perspective view of a food storage container 300 at least partially formed from antimicrobial article 100 (shown in FIG. 1). In the exemplary embodiment, container 300 includes a front wall 302, a rear wall 304, a first sidewall 306, a second sidewall 308, a bottom wall 310, and a cover 312. Walls 302-312 together define a cavity 314 within container 300 in which an item, for example a food item, is meant to be stored. In the exemplary embodiment, container 300 includes removable cover 312. Alternatively, container 300 is a five-sided container not having a cover. Generally, container 300 is any structure in which items may be placed for storage, preservation, and decontamination.

In the exemplary embodiment, each of walls 302-312 is formed from antimicrobial article 100 such that any food placed within cavity 314 is surrounded by antimicrobial article 100. Alternatively, fewer than all of walls 302-312 are formed from antimicrobial article 100. For example, in one embodiment, only bottom wall 310 is formed from antimicrobial article 100. In such a configuration, any other walls of container 300 are formed from any material. Generally, at least one of walls 302-312 is formed from antimicrobial article.

In operation, food meant for consumption, or any other perishable item, is placed within container 300 having at least one of walls 302-312 formed from antimicrobial article 100. The "impact zone effect" of antimicrobial article 100, as described above, effectively neutralizes a majority of the pathogens that cause the food items to begin to decay. As such, food items stored in container 300 decay at a much slower rate than when not exposed to the "impact zone effect" of antimicrobial article 100, and food items with a relatively short shelf life, such as fruits, may be stored in container 300 in an edible state for a much longer period of time before consumption.

Alternatively, other items exposed to potentially harmful pathogens, such as, but not limited to surgical equipment and smartphones, may be stored in container 300 for a period of time to eliminate such pathogens in a similar manner.

Experimental Data

A prototype of the antimicrobial article described above utilizing an antimicrobial alloy core of at least 70% molybdenum was tested by an independent testing laboratory using the pathogen *listeria monocytogenes* ATCC 23074. The results showed the pathogen strain was reduced by 99% in approx. 100 minutes on the prototype antimicrobial article tested at $1.2 \times 10^3$ cells [1200 cells] at time 0. The pathogen directly contacted with the molybdenum alloy core, and was neutralized by the "oligodynamic effect".

In another experiment, exposed molybdenum and ASTM A240 TP 316L stainless steel antimicrobial alloy were exposed to *E. coli* O157:H7 ATTC 43895 for a time period of 3 hours and measurements of the number of pathogen cells remaining were conducted at regular time periods. At relatively low population densities (<4,000 cells), the exposed molybdenum and stainless steel antimicrobial alloy, showed significant population reduction of *E. coli* O157:H7 ATCC 43895. Specifically, the exposed molybdenum and stainless steel antimicrobial alloy showed a greater than 4 log pathogen reduction in the population within 45 minutes.

The above described antimicrobial article facilitates efficient methods of disinfecting a surface. Specifically, the antimicrobial article described herein includes an antimicrobial core including molybdenum. The antimicrobial core includes an alloy of at least 50% molybdenum, with the remaining portion of the core including a non-antimicrobial alloy, such as nickel, zinc, or stainless steel. In the above described embodiment, a top surface of the core is exposed to the environment such that any potentially harmful bacterium and pathogens coming into contact with the top surface are eliminated within a relatively short period of time, for example, within 2 hours of exposure to top surface 104 of core 102 due to the "oligodynamic effect" described herein. Furthermore, in embodiments where the antimicrobial core is not exposed, the electromagnetic energy produced by the antimicrobial core eliminates potentially harmful bacterium and pathogens within a known distance of the antimicrobial core due to the "impact zone effect" described herein.

Exemplary embodiments of methods, systems, and apparatus for using an antimicrobial article are not limited to the specific embodiments described herein, but rather, components of articles and steps of the methods may be utilized independently and separately from other components and steps described herein. For example, the antimicrobial article may be used in combination with other application environments and in other procedures, and is not limited to practice with the systems or methods described herein. Rather, the exemplary antimicrobial article can be implemented and utilized in connection with many other applications, equipment, and systems that may benefit from the advantages described herein.

Although specific features of various embodiments of the disclosure may be shown in some drawings and not in others, this is for convenience only. In accordance with the principles of the disclosure, any feature of a drawing may be referenced and claimed in combination with any feature of any other drawing.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An antimicrobial article comprising an antimicrobial core comprising a first surface and an opposing second surface, wherein said antimicrobial core is formed from an antimicrobial alloy comprising greater than 60% by volume molybdenum such that said antimicrobial alloy is configured to eliminate pathogens located proximate said first and second surfaces.

2. The antimicrobial article in accordance with claim 1, wherein said antimicrobial alloy comprises an antimicrobial active component and a non-antimicrobial inactive component, wherein said antimicrobial active component comprises molybdenum.

3. The antimicrobial article in accordance with claim 2, wherein said antimicrobial alloy comprises a range of approximately 1% to approximately 40% by volume said non-antimicrobial inactive component.

4. The antimicrobial article in accordance with claim 2, wherein said non-antimicrobial inactive component comprises at least one of nickel, zinc, and stainless steel.

5. The antimicrobial article in accordance with claim 4, wherein said antimicrobial alloy comprises approximately 70% by volume molybdenum and approximately 30% by volume nickel.

6. The antimicrobial article in accordance with claim 1, wherein said antimicrobial alloy comprises a range of approximately 60% to approximately 99% by volume molybdenum.

7. The antimicrobial article in accordance with claim 1, further comprising an adhesive layer coupled to one of said first surface and said second surface, said adhesive layer configured to couple said antimicrobial core to an object.

8. The antimicrobial article in accordance with claim 7, further comprising a sheeting layer removably coupled to said adhesive layer.

9. The antimicrobial article in accordance with claim 1, further comprising a protective coating coupled to one of said first surface and said second surface.

10. The antimicrobial article in accordance with claim 9, wherein said protective coating is removable from said antimicrobial core.

11. The antimicrobial article in accordance with claim 9, wherein said protective coating is fixedly coupled to said antimicrobial core.

12. The antimicrobial article in accordance with claim 9, further comprising an adhesive layer coupled to a remaining one of said first surface and said second surface.

13. An antimicrobial article comprising an antimicrobial core comprising a first surface and an opposing second surface, wherein said antimicrobial core is formed from an antimicrobial alloy comprising molybdenum and a non-antimicrobial inactive component comprising stainless steel such that said antimicrobial alloy is configured to eliminate pathogens located proximate said first and second surfaces.

14. The antimicrobial article in accordance with claim 13, wherein said antimicrobial alloy comprises at least 50% by volume molybdenum.

15. The antimicrobial article in accordance with claim 14, wherein said antimicrobial alloy comprises less than 50% by volume stainless steel.

16. The antimicrobial article in accordance with claim 13, wherein said antimicrobial alloy comprises at least 60% by volume molybdenum.

* * * * *